United States Patent [19]

Becker et al.

[11] Patent Number: 4,657,538
[45] Date of Patent: Apr. 14, 1987

[54] PANTY LINER WITH FLOW RETARDING LAYER

[75] Inventors: Patricia E. Becker, Manalapan Township, Monmouth County; Kenneth J. Molee, Hightstown, both of N.J.

[73] Assignee: Personal Products Company, Milltown, N.J.

[21] Appl. No.: 760,004

[22] Filed: Jul. 29, 1985

[51] Int. Cl.4 ............................................ A61F 13/16
[52] U.S. Cl. ................................... 604/381; 604/378
[58] Field of Search .............. 604/381, 378, 384, 385, 604/365, 374, 375, 376, 377

[56] References Cited

U.S. PATENT DOCUMENTS 4,518,451  5/1985  Luceri et al. .................. 604/378 X Primary Examiner—John D. Yasko
Attorney, Agent, or Firm—Jason Lipow

[57] ABSTRACT

A product for absorbing body fluids intended to be worn in the crotch portion of the undergarment is provided. The product includes a first absorbent layer at the side nearest the body and a second absorbent at the side facing the garment. The layers have therebetween liquid flow retarding means to retard liquid from passing from one absorbent layer to the other. The liquid retarding means comprise one or more plies of a web of hydrophobic fiber which web has a rising column strike through value of at least 10 inches of water and an air permeability of at least 20 cubic feet per foot squared per minute.

11 Claims, 5 Drawing Figures

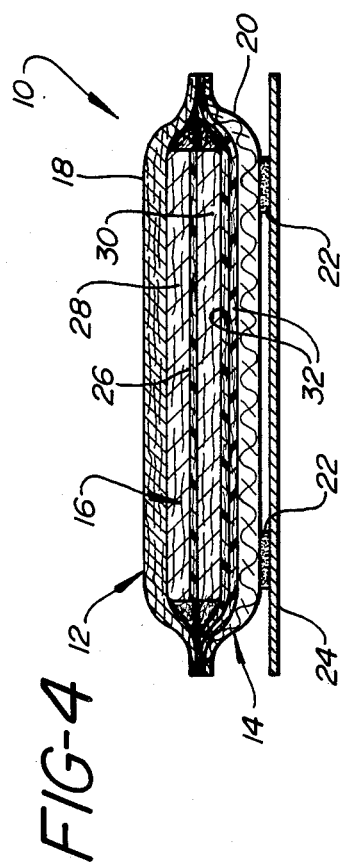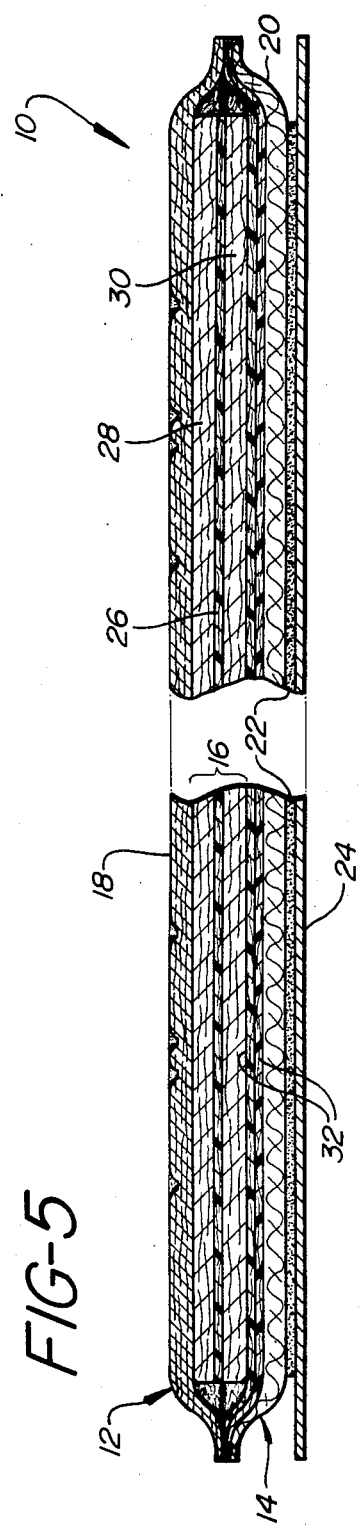

PANTY LINER WITH FLOW RETARDING LAYER

BACKGROUND OF THE INVENTION

This invention relates to thin absorbent panty liners for protecting the wearer's undergarment both during intermenstrual use and, alone or in conjunction with other catamenial devices, during menstrual use.

Several products are now on the market to provide the user with protection from the staining of undergarments and, in general, are designed to be worn in the crotch portion of an undergarment. These products comprise a body facing side, pervious to body fluids; an absorbent body which is capable of absorbing and retaining quantities of body fluid and a fluid impermeable backing on the garment facing side of the product for preventing the fluid absorbed and retained from "striking through" onto the crotch surface of the undergarment. Additionally, these products have generally been provided with a layer of pressure-sensitive adhesive for adhering the product to the crotch portion of the garment.

One such product has been described in our co-pending U.S. patent application Ser. No. 423,389 filed on Sept. 24, 1982 which product has the added feature of breathability. As disclosed in the specification of this application, the panty liner described is required to hold relatively little fluid when used intermenstrually or when used in conjunction with other catamenial devices. However, as such product is meant to be worn for a considerable length of time, it is desirable that the product be capable of drying between fluid deposits. As described in the above-referenced disclosure, this is accomplished by designing the product to have a repellent, air permeable barrier on the garment facing side in conjunction with maintaining overall air permeability of the product to at least a minimum value. While "breathable" barriers have been known and suggested, this product was the first to be designed to provide overall breathability, in that the importance of this parameter, in products of this nature, is believed to have been recognized by the inventors for the first time.

The above-described product has performed efficiently when the use conditions for which it was designed occur, i.e., low volume deposits of body fluids. Unfortunately, on occasion the wearer experiences an unusually large discharge of fluid concentrated in a rather small area of the panty liner. In these instances, the panty liner fails to perform its function in that such fluid deposits pass directly from the body facing side of the permeable cover, through the absorbent layer and then through the breathable barrier and onto the undergarment.

There is therefore, a need to address this problem of strike through under unusually large deposition conditions, without sacrificing the other desirable aspects of the breathable panty liner.

SUMMARY OF THE INVENTION

In accordance with the teachings of this invention, a panty liner is provided with a means for minimizing strike through under unusually heavy liquid deposition without sacrificing the desirable attributes of breathability.

Specifically provided is a product for absorbing body fluids which includes a first absorbent layer at the side nearest the body and a second absorbent layer at the side facing the garment, said layers having therebetween liquid flow retarding means which will retard liquid from passing from the body side absorbent layer to the garment side absorbent layer and instead will direct fluid laterally within the body side absorbent layer. It is only after considerable fluid has been deposited and distributed laterally within the body side absorbent layer that fluid will pass through the flow retarding means and into the garment side absorbent layer.

The retarding means comprise one or more plies of a web of hydrophobic fibers which web has a Rising Column Strike Through (RCST) Value of at least 10 inches of water. Preferably the RCST Value is at least 12 inches of water. Additionally, to maintain the product breathable and to utilize the garment side absorbent layer, the retarding means must also have an air permeability of at least 20 $ft^3/ft^2$/min and preferably at least about 40 $ft^3/ft^2$/min as measured by the Frazier Air Permeometer as described herein.

BRIEF DESCRIPTION OF THE DRAWINGS

The invention will be best understood by consideration of the following description taken together with the attached drawings in which:

FIG. 4 is a transverse cross-sectional view of the panty liner of FIG. 2, taken through line 4—4; and FIG. 5 is a longitudinal, cross-sectional view of the panty liner of FIG. 2, taken through line 5—5.

DETAILED DESCRIPTION OF THE INVENTION

Figure 1:
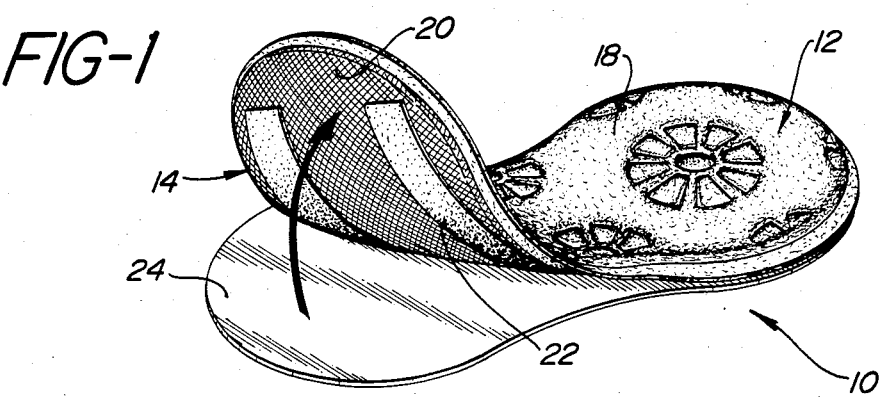
FIG. 1 is a perspective view of a panty liner incorporating the teachings of this invention with the adhesive protecting release layer being partially removed for clarity.
Figure 2:
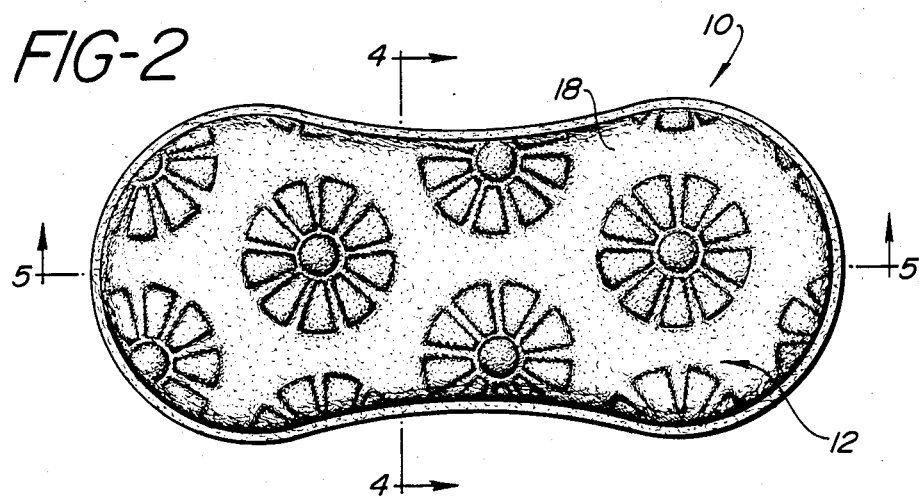
FIG. 2 is a plan view of the body facing side of the panty liner of FIG. 1.

FIGS. 1–5 illustrate, in perspective, plan and cross-sectional views, a panty liner 10 incorporating the teachings of this invention. As best viewed in FIGS. 2 and 3, respectively, the panty liner comprises a body facing side 12 and a garment facing side 14. The outer body facing side of the liner consists of an outer cover 18 which may or may not be capable of absorbing and retaining body fluids but, in any event, is permeable by such body fluids. The outer most surface of the body facing side of the liner 10 is provided with an aesthetically pleasing pattern of depressed areas which penetrates into the cover 18 and may also penetrate into one or more of the core material plies 16.

The outer cover 18 may be any of the typical fluid pervious materials used as covers for sanitary napkins such as a woven cover, e.g., gauze or, for example, a nonwoven material such as the ones described in U.S. Pat. No. 3,554,788 issued on Jan. 12, 1971 to M. R. Fechillas, which has the added advantage of being flushable, i.e., may be disposed of by dispersing and flushing away in a water closet.

The outer cover may also comprise a low density, highly absorbent, thermal bonded fabric comprising a mixture of absorbent fibers and staple length polyester/-polyethylene conjugate fibers. The absorbent fibers are preferably wood pulp or other cellulosics which may have been treated to enhance absorbency. The conjugate fibers are fibers which comprise a polyester core surrounded by a sheath of polyethylene.

Preferably, the conjugate fibers employ high density polyethylene, that is, linear polyethylene that has a density of at least 0.94 and a Melt Index (as determined by ASTMD-1238E method, employing the parameters of 190° C. and 2160 gms) of greater than 1, preferably greater than about 10, and more preferably from about 20 to about 50. The fibers may comprise from about 40 to 60 percent, by weight polyester and, preferably, from 45 to 55 percent by weight polyester, with the remainder being polyethylene. Such fibers may be used in deniers of from 1 to about 6 and may be from about ½ inch (1.27 cm.) to about 3 to 4 inches (7.62 to 10.16 cms.) long. Preferably the fabric comprises outer layers of heat fusible fibers having the mixture of wood pulp and conjugate fibers sandwiched therebetween. Such outer layers may consist of the conjugate fibers or may in fact be any heat-fusible material such as polypropylene fibers, for example. The fabric is stabilized by applying heat thereto under essentially zero pressure whereby thermal bonding takes place without destroying the integrity of the fibers and a low density for the fabric is maintained. Typically, the bulk density of such fabrics is less than about 0.15 grams per cubic centimeter.

In a preferred embodiment, the outer cover 18 contains sufficient quantities of a heat sealable component, e.g., polypropylene or polyethylene, so that the cover 18 may be sealed to a backing 20 to fully enclose the product 10. In this connection, the backing 20 may be any heat sealable, relatively open fabric and has the primary function of cooperating with the outer cover 18 to contain the remaining elements of the liner. One particularly useful backing material comprises two layers; the first consisting of polyester and the other consisting of the conjugate fibers described in connection with the cover material 18. The fabric may be manufactured by depositing a layer of polyester fibers onto a moving screen and laying the conjugate fibers thereover. The fabric may get its integrity by entangling these fibers utilizing a process similar to that described in U.S. Pat. No. 3,485,706 issued on Dec. 23, 1969 to F. J. Evans. This process lends itself to producing a fabric having a regular pattern of apertures therethrough which is particularly suitable for use as a backing material in the breathable panty liner of this invention. For simplicity, where the sealing properties of the conjugate fibers are not required, the backing may comprise only the polyester fibers.

It will be understood that while it is preferred that the outer cover 18 and the backing contain heat sealable material and be sealed together by heat sealing, such is not essential. For example, the backing and cover may comprise merely cellulosic fibers and may be sealed together by use of adhesives, crimping or combinations thereof.

Figure 3:
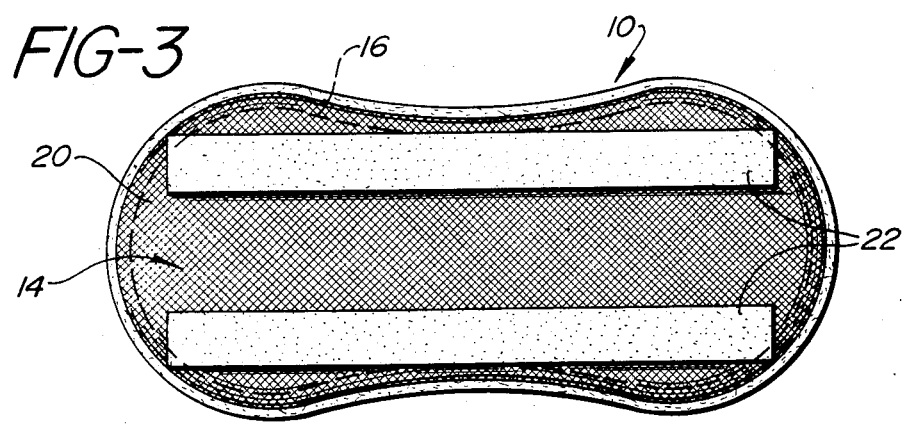
FIG. 3 is a plan view of the garment facing side of the panty liner of FIG. 1.

Overlying one or more areas on the outer surface of the backing layer 20 are adhesive layers 22 comprising pressure-sensitive adhesive for adhering the panty liner to the crotch portion of the wearer's undergarment. As best illustrated in FIG. 3, such areas comprise two longitudinally extending bands of pressure-sensitive adhesive although it will be understood by those skilled in the art that many variations in the number and shape of these adhesive areas are possible. The pressure-sensitive adhesive may be any of the already known compositions suitable for this purpose including, for example, the water based pressure-sensitive adhesives such as the acrylate adhesives, e.g., vinyl acetate-2 ethyl hexyl acrylate copolymer which is generally combined with tackifiers such as, for example, ethylene amine. Alternatively, the adhesive may comprise the rapid setting thermoplastic (hot melt) adhesives such as block copolymers exemplified by styrene and butadiene/styrene copolymers. The adhesive area may also comprise a two-sided adhesive element.

As is best illustrated in FIGS. 1, 4 and 5, the adhesive areas 22 are protected by a release strip 24 to avoid undesired adhesion prior to use. The release strip 24 may be made of any suitable sheet-like material which adheres with sufficient tenacity to the adhesive areas 22 to remain in place, but which can be readily removed when the panty liner 10 is to be used. A particularly useful material is a semi-bleached kraft paper, the adhesive contacting side of which has been silicone coated to provide for easy removal from the adhesive just prior to use.

In accordance with the teaching of this invention, contained between the cover 18 and the backing 20, as best viewed in FIGS. 4 and 5, is core 16. Core 16 comprises a flow retarding means 26 sandwiched between a body side absorbent layer 28 and a garment side absorbent layer 30. It will be understood that while the body side absorbent layer 28, the garment side absorbent layer 30 and the retarding means 26 are each shown in the specific embodiment illustrated in the drawings as a single ply, it is within the contemplation of this invention to have these layers comprise multiple plies provided the teachings herein are met.

The absorbent layers 28 and 30 may be comprised of a variety of materials known and used as absorbents in products of this nature and, for example, may include fibrous webs of wood pulp, rayon or other cellulosic materials as well as synthetic fibers or foam materials such as polyester fibers, or polyurethane foams. These layers any also be mixtures of the above and may also include absorbent enhancers such as the hydrocolloidals or superabsorbent materials as are suggested in the art.

A suitable material for layers 28 and 30 is that recited in U.S. Pat. No. 3,663,238 issued on May 16, 1972 to G. J. Liloia, et al. Described therein is a soft, lofty nonwoven comprising a mixture of approximately 25%, by weight, of relatively long (about 2.9 cm.) rayon fibers and about 75%, by weight, of short (about 0.2 cm.) wood pulp fibers and being stabilized by through bonding with a water dispersible binder present in an amount of between about 1% and about 30% of the weight of the fibers, on a dry basis. The binders of choice are the self-curing acrylic latex type, the urethane type or other similar binders.

Another suitable absorbent material for the layers 28 and 30 is the same thermal bonded, polyester/polyethylene conjugate fibers and wood pulp fabric described above in connection with cover 18.

Still another suitable absorbent material is simply a bonded web of wood pulp fibers and binder. For example, such a useful material is a web comprising, by weight, 80% wood pulp fibers and 20% binder and having a density of 0.072 gm/cc and a basis weight of about 2.5 oz/yd$^2$. The binder may be of the kind discussed above with the binders of choice being mixtures of polyvinyl acetate and polyacrylates.

In accordance with this invention, a flow retarding means, layer 26 is provided between the body side absorbent layer 28 and the garment side absorbent layer 30. The function of this flow retarding means is to preclude a sudden large surge of body fluid deposited on a relatively small area of the product from passing unhindered through the body side absorbent layer, into the garment side absorbent layer, overburdening the barrier system (breathable layers 32, 34), and thereby staining the wearer's undergarment.

Instead, because of the presence of the flow retarding means 26, such a sudden surge of fluid is retarded in flow from the body side to the garment side and instead is directed laterally and dispersed in the body side absorbent layer 28. On the other hand, the flow retarding means 26 must be capable of allowing for fluid flow therethrough, primarily so that fluid, in the form of vapor, may pass through the product and hence the product can quickly dry while being worn. Additionally, should the body side absorbent layer become heavily loaded with fluid, than it is important to have the capability of transporting such fluid through the flow retarding means and retaining such fluid in the garment side absorbent layer 30.

It has been discovered that these functions can be served by providing a flow retarding means such as a layer which comprises hydrophobic fibers having a Rising Column Strike Through Value of at least 10 inches of water and preferably at least 12 inches of water. Additionally the layer used as the flow retarding means must have a Frazier Air permeability of at least 20 $ft^3/ft^2/min$ and preferably at least 40 $ft^3/ft^2/min$.

The hydrophobic characterization of the fiberous layer is the term used in the art to characterize a material on which liquid will not spead and which has a contact angle greater than about 50°. The contact angle is the angle within the water drop between the water/air interface and the water/solid interface at the common junction of these two interfaces. The contact angle may be determined by using any of the procedures known in the art such as those detailed in Physical Chemistry of Surfaces, 2nd Ed. 1967 by A. Adamson. It will be understood that hydrophobicity may be achieved by employing inherently hydrophobic polymers to form the fibrous web such as polypropylene fibers or the like. Alternatively, hydrophilic fibers or webs made therefrom may be used if they have been treated to render them hydrophobic such as, for example, repellent treated tissue webs. Both types of webs may be employed as the flow retarding means in the product of this invention.

The web employed must have the ability to retard the flow of liquids and this character is quantified by a web having a Rising Column Strike Through Value of at least 10 inches of water and preferably at least 12 inches of water. The Rising Column Strike Through Value is obtained from a test which quantifies the resistance of a fabric or layer to the penetration of a liquid. As used herein, the test is performed using a vertically mounted clear plastic tube having an inside diameter of two inches, open at its top and bottom. The bottom is surrounded by a flange and a sample, supported on a plate having a two inch diameter hole, spanned by the sample, is clamped to the flange so that the hole in the plate is co-axial with the open end of the cylinder. The sample employed is square, measuring 3.5 inches on each side. Prior to insertion in the device the sample is conditioned by exposure to air at 65±2% relatively humidity and 70±2° F.

With the sample so affixed, water is introduced into the cylinder through an inlet port having a diameter of ¼ inch via a ¼ inch inlet tubing connected to a city water source. The bottom of the port is located 1.0 inch from the bottom of the cylinder. Water is introduced at a rate sufficient to fill the cylinder at a rate of 11.5±0.5 inches per minute. The bottom of the sample is observed and when the first drop of water is observed to have penetrated the sample, the water level in the cylinder is recorded as the Rising Column Strike Through Value in inches of water.

The web employed must also have a certain permeability in order to allow the product to be breathable as well as to allow liquids to pass from the body side absorbent layer to the garment side absorbent layer when the former is heavily loaded with liquid. Accordingly, the web should have an air permeability of at least 20 $ft^3/ft^2/min$ and preferably at least about 40 $ft^3/ft^3/min$ as measured by the Frazier Air Permeometer, model number 608, sold by Frazier Precision Instrument Company Inc., Gathersberg, Md. This device measures the flow rate of air in cubic ft/min necessary to develop a pressure drop of one half inch of water across the sample per square foot of sample area.

It will be understood by those skilled in the art that many different types of webs or layers may be prepared, and when such layers are prepared to meet the prescribed properties set out herein, they are usable in accordance with the teachings of this invention.

A particularly suitable material for use as the flow retarding means is one or more plies of a tissue paper which is treated by applying thereto a chemical agent which gives the tissue the required resistance to flow and hydrophobicity. Preferably, each ply of the untreated tissue comprises cellulose fibers held in place by hydrogen bonding. The basis weight may vary from about 0.2 to about 1.0 $oz/yd^2$ and stil more preferably from about 0.5 to about 0.75. The tissue should also have the requisite strength to maintain its integrity during the manufacture of the product.

The tissue should be treated with sufficient repellent treating agent to meet the criteria set out above. Several such repellent treating agents are available including for example, rosens; certain resins such as shellac, East India resins, Danner resins, sien, silicone resins, the condensation products of formaldehyde with phenols, urea and melamine; emulsion of urea; insoluble fatty acid (e.g., behenic acid); acetylating agents, e.g., acetic anhydride in an inert solvent; cyanoethylating agents; or diketenes (see for example U.S. Pat. No. 2,627,477) or polyketenes or copolymers of polyketenes. A particularly useful treatment is achieved by use of a repellent material obtained from the Hercules, Inc. of Wilmington, Del. and sold by them under the name, "Aquapel". This repellent comprises a mixture of alkyl ketene dimers having from 16 to 18 carbon atoms. The treatment may be carried out by passing the tissue through an aqueous bath containing the repellent. Additives may also be provided in the bath for the purposes of facilitating the process, stabilizing the active compounds or for coloring the repellent tissue for aesthetic purposes if so desired. Such additives may include for example, pH stabilizers, antifoaming agents, pigments and color stabilizers or the like.

Another useful material for employment as the flow retarding layer of the invention is a web comprised of synthetic hydrophobic polymer fibers, held together by virtue of being fusion bonded. Such a web may be made by heating an entangled mass of such fibers so as to melt them at the contacting points between adjacent fibers. Alternatively, the web may be formed at the time the fibers are extruded, by randomly forming the web while the fibers are still at least partially plastic. Examples of processes for manufacturing such webs are described in U.S. Pat. Nos. 3,595,245; 3,704,198; and 3,825,380. The fibers chosen should be thermoplastic synthetic polymers which are hydrophobic or which can be treated to be hydrophobic with polyethylene, polypropylene and polyester fibers being the materials of choice.

Referring again to FIGS. 4 and 5, interposed between the core 16 and the backing 20 are two plies of a breathable carrier material 32. This material conforms entirely with that described in our copending patent application Ser. No. 423,389 filed on Sept. 24, 1982, and is incorporated herein by reference. Basically, this material 32 is a fibrous, vapor permeable, liquid repellent layer for protecting the undergarment of the wearer from body fluids while allowing evaporated body fluids to pass therethrough. The material 32 should have a degree of repellency of at least 3.0 cm. of water and an air permeability of at least 20 ft$^3$/ft$^2$/min. The choice of materials for material 32 may vary widely within these teachings but the same materials as described in conjunction with the flow retarding means 26 are suitable for use as materials 32.

EXAMPLE 1

The following example illustrates the advantages of the teachings of this invention.

A first series of panty liners are prepared having the general configuration and shape as illustrated in FIGS. 1-5. The product has a length of 5.5 inches (14.0 cms.), a width of 2.2 inches (5.6 cms.), a minimum width of 1.85 inches (4.7 cms.) and a maximum thickness of 0.21 inches (0.533 cm.). The product has an overall weight of 2.47 gms. The body facing side of the liner is provided with an outer cover constructed of a thermal bonded absorbent fabric comprising, overall, 24% by weight of wood pulp fibers and 76% by weight of conjugate fibers having a polyester core and a high density polyethylene sheath. The conjugate fibers have a staple length of 3.81 cms. and a denier of 3.0. The materials are so distributed as to provide a pulp/conjugate fiber mixture sandwiched between two veneers of conjugate fibers, the veneers having basis weights of 0.32 oz./yd$^2$. and 0.37 oz./yd$^2$., the heavier veneer ultimately being employed on the body facing side of the product. The fabric is stabilized by passing hot air through the fibers and thereby melting the high density polyethylene which bonds the fibers together upon cooling. The overall fabric has a basis weight of 1.55 oz./yd$^2$.

The absorbent core of the liner comprises a body side absorbent layer and a garment side absorbent layer surrounding, therebetween, a flow retarding means.

Both the body side absorbent layer and the garment side absorbent layer are bonded webs comprising 80% by weight wood pulp fibers and 20% by weight of polyvinyl acetate/polyacrylate binder. Each layer has a density of 0.072 gm/cc and a basis weight of 2.5 oz./yd$^2$.

The flow retarding means is a single ply of a web comprising polypropylene fibers. This web is made in accordance with the processes described in U.S. Pat. Nos. 3,595,245; 3,704,198 and 3,825,380. The web is obtained from the Riegel Division of James River Corporation of Milford, N.J. and has a basis weight of 0.59 oz./yd$^2$., a thickness of 0.0079 inches, a tensile strength of 1.32 lbs./in./ply, and an elongation to break of 45.6%.

The product utilizes, as a backing, the wholly polyester fiber apertured entangled fabric described above. Two plies of the same material utilized as the flow retarding means are employed as a breathable barrier.

A second series of liners are made with the exception that the flow retarding means are omitted. The products are tested by two panels of thirty women each wherein one panel is provided with the liners having the flow retarding means and the second panel is provided with the liners without the flow retarding means. Each liner, prior to submission to a panelist, has deposited centrally thereon, 0.5 cubic centimeters of ersatz menstrual fluid. The panelist wears the product, as in normal daytime wear, for four hours. The samples are collected and visually examined for strike through. The results are shown in Table 1 below.

TABLE 1

| Product | No. of Panelists | Products With Strike Through Failures (%) |
| --- | --- | --- |
| Without Flow Retarding Means | 30 | 96.6 |
| With Flow Retarding Means | 30 | 41.3 |

As can be seen from the above table, the flow retarding means of this invention has greatly inhibited strike through failures.

EXAMPLE 2

To illustrate the importance of the inclusion of a flow retarding means having the properties prescribed herein the following procedure was carried out. A core is assembled comprising a body side absorbent layer and garment side absorbent layer, using materials described in connection with the foregoing example, and having, therebetween various materials as flow retarding means. All components were cut to 4 inches by 4 inch squares and each sample tested varied from the others only by virtue of the varied flow retarding means. Samples 1 through 6 were prepared wherein, in Sample 1 the flow retarding means employed is that described in connection with Example 1 and conforms to the teachings of this invention. In Sample 2, the flow retarding means employed is two plies of the flow retarding means of Sample 1 and also conforms to the teachings of this invention. In Sample 3, the flow retarding means employed is three plies of repellent treated tissue, each ply of which is made from untreated creped tissue having a basis weight of 0.63 oz./yd.$^2$/ply and having been treated in an aqueous bath incorporating a repellent material sold by the Hercules Chemical Company as Aquapel 360XC. Sample 3 also conforms to the teachings of this invention. In Sample 4, the flow retarding means employed is one ply of a melt blown polypropylene web which has been treated with a surfactant to be hydrophilic. This material does not conform to the teachings of this invention. In Sample 5, the flow retarding means consists of 24 plies of the same material as Sample 4, and likewise, does not conform to the teachings of this invention. Finally, Sample 6 omits any material as a flow retarding means.

The test is conducted by depositing 5 cubic centimeters of an ersatz menstrual fluid onto the exterior surface of the body side absorbent layer. A five pound weight is placed on this surface for one minute. The layers are disassembled and visually examined to ascertain the distribution of fluid. The results are shown in Table 2 below.

TABLE 2

| Sample | Flow Retarding Means | Hydrophobicity | RCST (in. of H$_2$O) | Air Permeability (ft$^3$/ft$^2$-min) | Results |
|---|---|---|---|---|---|
| 1 | One Ply Polypropylene Web | Hydrophobic | 14 | 101 | Fluid in body facing absorbent layer only |
| 2 | Two Plies Polypropylene Web | Hydrophobic | 27 | — | Fluid in body facing absorbent layer only |
| 3 | Three Plies Repellent Tissue | Hydrophobic | 14.6 | 63 | Fluid in body facing absorbent layer only |
| 4 | One Ply Polypropylene Web with wetting agent | Hydrophilic | 0 | 239 | Approximately equal amounts of fluid in both absorbed layers |
| 5 | 24 Plies of Polypropylene Web with wetting agent | Hydrophilic | 0 | 7.5 | Approximately equal amounts of fluid in both absorbed layers |
| 6 | No flow retarding means | — | — | — | Approximately equal amounts of fluid in both absorbed layers |

As can be seen, all flow retarding means conforming with the teachings of this invention (Samples 1–3, inclusive) retained fluid in the body side absorbent layer and retard flow into the garment side absorbent layer. On the other hand, the nonconforming samples (4–6, inclusive) resulted in an approximately equal distribution of fluid in both absorbent layers.

What is claimed is:

1. A product for absorbing body fluids comprising a body side absorbent layer, a garment side absorbent layer and having therebetween a liquid for retarding means for retarding the flow of liquid from passing from said body side absorbent layer to said garment side absorbent layer; said liquid flow retarding means comprising one or more plies of a web of hydrophobic fibers, said means having a Rising Column Strike Through Value of at least 10 inches of water and an air permeability of at least 20 ft$^3$/ft$^2$—min.

2. The product of claim 1 wherein said means has a Rising Column Strike Through Value of at least 12 inches of water.

3. The product of claim 1 wherein said means has an air permeability of at least 40 ft$^3$/ft$^2$/min.

4. The product of claim 1 wherein said means exhibits a contact angle of greater than 50°.

5. The product of claim 1 wherein said means comprise a web of synthetic polymeric fusion-bonded fibers.

6. The product of claim 5 wherein said means comprises polypropylene fibers.

7. The product of claim 1 wherein said means comprise hydrophilic fibers treated to be hydrophobic.

8. The product of claim 7 wherein said means comprise treated cellulosic fibers.

9. The product of claim 8 wherein said means comprise tissue treated with repellant treating agent.

10. A panty liner to be worn in the crotch portion of an undergarment comprising:
    a central core having a body facing side and a garment facing side;
    said central core having a body side absorbent layer, a garment side absorbent layer and a liquid flow retarding means therebetween;
    said liquid flow retarding means comprising one or more plies of a web of hydrophobic fibers, said means having a Rising Column Strike Through Value of at least 10 inches of water and an air permeability of at least 20 ft$^3$/ft$^2$/min;
    the garment facing side of said core having a barrier layer for protecting said undergarment.

11. The panty liner of claim 10 wherein said barrier layer comprises at least one ply of vaper permeable, liquid repellent material said ply having a repellency of at least 3.0 cm. of water and an air permeability of at least 20 ft$^3$/ft$^2$/min.

* * * * *